United States Patent [19]

Dickhardt et al.

[11] Patent Number: 5,245,008
[45] Date of Patent: Sep. 14, 1993

[54] PROCESS FOR THE PURIFICATION OF INSULINS BY CHROMATOGRAPHY

[75] Inventors: Rainer Dickhardt; Bernhard Unger, both of Kelkheim; Leonhard Häfner, Königstein, all of Fed. Rep. of Germany

[73] Assignee: Hoechst Aktiengesellschaft, Frankfurt am Main, Fed. Rep. of Germany

[21] Appl. No.: 754,003

[22] Filed: Sep. 3, 1991

[30] Foreign Application Priority Data

Sep. 5, 1990 [DE] Fed. Rep. of Germany ....... 4028120

[51] Int. Cl.$^5$ ............................ C07K 1/14; C07K 7/40
[52] U.S. Cl. ..................................... 530/305; 530/344
[58] Field of Search ................................ 530/305, 344

[56] References Cited

U.S. PATENT DOCUMENTS

| | | | |
|---|---|---|---|
| 4,129,560 | 12/1978 | Zoltobrocki | 530/305 |
| 4,601,852 | 7/1986 | Obermeier et al. | 530/303 |
| 4,677,192 | 6/1987 | Obermeier et al. | 530/305 |

FOREIGN PATENT DOCUMENTS

| | | |
|---|---|---|
| 3147842 | 6/1983 | Fed. Rep. of Germany . |
| WO89/01485 | 2/1989 | PCT Int'l Appl. . |
| 1582056 | 12/1980 | United Kingdom . |
| 2119248 | 11/1983 | United Kingdom . |

OTHER PUBLICATIONS

Journal of Chromatography, vol. 256, issued 1983, Parman, "Comparison of Carboxymethyl-Cellulose . . . ", pp. 293-301.

Chemical Abstract 88:177,670m, Shataeva et al., "Thermodynamics of Polyfunctional Interchanges during Ionic Exchange", (1975).

Welinder et al., "Reversed-Phase High-Performance Liquid Chromatography of Insulin: Resolution and Recovery in Relation to Column Geography and Buffer Components", J. Chromatography, vol. 361, pp. 357-367 (1986).

*Primary Examiner*—Jeffrey E. Russel
*Attorney, Agent, or Firm*—Finnegan, Henderson, Farabow, Garrett & Dunner

[57] ABSTRACT

A process for the purification of insulins and insulin derivatives by chromatography in aqueous, buffered solvents which contain water-miscible organic solvents, on lipophilically modified silica gel, is described, wherein the aqueous, buffered solvents contain zwitterions, or the pH of the solvent mixture is in the vicinity of the isoelectric point of the insulin or insulin derivative to be purified and zwitterions are present.

6 Claims, No Drawings

PROCESS FOR THE PURIFICATION OF INSULINS BY CHROMATOGRAPHY

The invention relates to a process for the purification of insulin and/or insulin derivatives by chromatography in aqueous, buffered solvents which contain water-miscible organic solvents, on lipophilically modified silica gel, with zwitterions being dissolved in the aqueous, buffered solvent and/or the pH of the solvent being in the vicinity of the isoelectric point of the insulin or insulin derivative to be purified.

The purification of insulins or insulin derivatives on lipophilically modified (reversed phase) silica gels is known from analytical separation methods and has been used successfully for many years in high-pressure liquid chromatography (HPLC) (W. S. Welinder et al., J. Chrom., 361, (1986) 357-367). On the analytical scale, amounts of protein in the µg range are loaded onto a column which is packed with modified silica gel and is made of steel, glass or plastic, and are then eluted by a flowing liquid mixture (usually acidic, aqueous buffer solutions with a constant or variable organic solvent concentration). The protein loading in this case is far less than 30 µg/ml of column volume.

Purification processes to date often use the solvents which are employed in the laboratory and are relatively toxic (acetonitrile) and corrosive, costly buffer components, for example tetraalkylammonium salts, alkylsulfonates, hexafluoroacetone, trifluoroacetate (E. P. Kroeff et al., J. Chrom., 461, (1989), 45-61). These mobile phases do not, when the mixtures are more heavily contaminated with insulin-like substances, result in satisfactory preparative separation in terms of quality, yield of the main component and overall recovery (J. Rivier, R. McClintock; J. Chrom., 268 (1983) 112-119; Peter et al., J. Chrom. 408 (1987) 43-52).

Insulins from previous chemical transformations such as, for example, from strongly acidic ester cleavages or enzymatic (trans-)peptidation processes, from purifications by ion exchange chromatography, by choosing particular pH values, if the electrical charge differences are sufficient (U.S. Pat. No. 4,129,560). The disadvantage of this method is the dilution effect and thus loss of valuable materials in the supernatants on working up the precipitates, the relatively long cycle time or that the overall recovery and thus the yield is lower.

It is possible in principle to achieve preparative separations by enlarging the column contents, the amount loaded and the throughput of eluent. The amounts of organic solvent required for this are, for example in the case of columns with diameters ≦20 cm, on the m³ scale. Solvents used for analytical HPLC (for example acetonitrile, DMF, methanol, dioxane etc.) are toxic so that use of these methods on the industrial preparative scale requires elaborate protective measures.

The object of the present invention was to develop a process for the purification of insulins and insulin derivatives by chromatography, in which the biological activity of the insulins is retained, high purities are achieved with one chromatography step, short cycle times, columns with useful lives of more than 50 chromatography cycles, regeneration of the stationary silica gel phase without time-consuming packing processes and the use of non-toxic solvents is achieved, so that an industrial preparative scale is possible.

A process has now been found to allow insulin and insulin derivatives to be purified by chromatography in aqueous, buffered solvents which contain water-miscible organic solvents, on lipophilically modified silica gel, wherein zwitterions are dissolved in the buffered solvents, or the pH of the solvent is in the vicinity of the isoelectric point of the insulin or insulin derivative to be purified and zwitterions are present.

Surprisingly, the presence of zwitterions, or chromatography at a pH of the solvent which is in the vicinity of the isoelectric point of the insulin or insulin derivative to be purified and the presence of zwitterions, results not only in good separation of required product and impurities but also good detachment of the proteins from the stationary phase (lipophilically modified silica gel). The separations which are achieved allow even insulin solutions which are heavily contaminated with insulin-like components to be purified, such as, for example, the separation of the A21-deamidoinsulin from insulin and insulin derivatives. Furthermore, the favorable detachment of the proteins from the solid phase means that the column packings have long useful lives, and makes possible a high overall recovery rate of the insulins.

The invention thus relates to a process for the purification of insulin and/or insulin derivatives by chromatography in aqueous, buffered solvents which contain water-miscible organic solvents, on lipophilically modified silica gel, wherein zwitterions are dissolved in the buffered solvents, or the pH of the solvent mixture is in the vicinity of the isoelectric point of the insulin or insulin derivative to be purified and zwitterions are present.

It is possible to employ in the process according to the invention all insulins such as, for example, insulins of all species which are of animal or human origin, insulin precursors such as, for example, proinsulins or pre-proinsulins, or recombinant insulins or insulin derivatives which are expressed by genetically modified microorganisms. It is also possible furthermore to employ insulin derivatives which have been prepared, for example, by chemical or enzymatic derivatization, for example De-Phe-B1-insulin, insulin-β-ketene-sulfonate, diarginine-insulin (B31, B32), monoarginine-insulin or diphenylalanine-insulin (B31, B32) (U.S. Pat. No. 4,601,852).

Preferably employed are insulin derivatives of the formula I

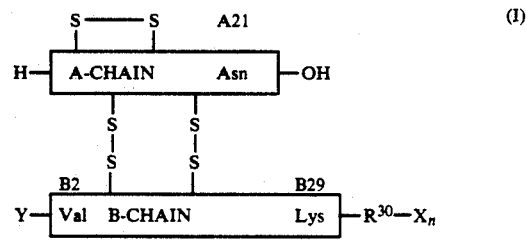

in which
R³⁰ is the residue of a genetically encodable L-amino acid,
X is a hydroxyl group, a physiologically acceptable organic group which is basic in nature and has up to 50 carbon atoms, a genetically encodable L-amino acid whose terminal carboxyl functionality which is present where appropriate can be free, an ester functionality, an amide functionality, a lactone or reduced to $CH_2OH$, n is an integer from 0 to 10,
y is hydrogen or L-phenylalanine, and the A and B chains are the sequences of animal or human insulin. Particularly preferably employed are insulin derivatives of the formula I in which R$^+$ is L-alanine or L-threonine and X is one or more L-amino acids from the group comprising L-arginine, L-lysine or L-phenylalanine.

The insulins and insulin derivatives can be employed both in relatively impure state and in prepurified form (for example by gel chromatography). After multiple crystallization and even after gel chromatography, insulin is still contaminated with insulin-like concomitants which have very similar molecular weights and which at appropriately chosen pH differ in their state of charge from one another and from insulin but form complexes with insulin (U.S. Pat. No. 4,129,560). Examples of such substances are deamidoinsulins, arginine- and diarginine-insulin, insulin ethyl ester and others.

A lipophilically modified silica gel means a silica gel onto which a hydrophobic matrix has been attached. Examples of a hydrophobic matrix are alkanes with a chain length of 3 to 20 carbon atoms. Examples of particularly preferred lipophilically modified silica gel materials are:

®Nucleosil, supplied by Macherey & Nagel: spherical and non-spherical materials with various particle sizes up to 45 μm, 100 Å pore width, C8- or C18-modified.

®Lichroprep, supplied by Merck: non-spherical and spherical materials with various particle sizes up to 40 μm, 60-250 Å pore width, C8-C18-modified;

®Lichrospher Select B, supplied by Merck: spherical material with particle size up to 25 μm, C8-modified;

®Waters Prep, C18-modified, 50-105 μm non-spherical, 100 Å pore width;

®Zorbax Pro10, supplied by DuPont: C8-modified, 10 μm, spherical, 100 Å pore width;

®Kromasil, supplied by EKA Nobel: C4-, C8-C18-modified, up to 16 μm, spherical, 100, 150 or 200 Å pore width.

Zwitterions are compounds which are able to take up and to eliminate protons, that is to say form cations in acidic solution and anions in alkaline solution, such as, for example, α-amino acids, betaine or betaine derivatives. Preferred zwitterions are glycine, glutamine or betaine (N,N,N-trimethylglycine). Glycine is particularly preferred.

The isoelectric point (IEP) of an insulin or insulin derivative is that pH of a solution of the insulin at which the number of cationic charges and anionic charges of the dissolved insulin equals zero. For example, the IEP of pig insulin is between pH 5.3 and 5.4 (H. Neurath, K. Bailey, Protein Hormones, Vol. II/A, The Proteins, page 636). The term "in the vicinity of the isoelectric point" means, in particular, pH values about 1 pH unit above or below the IEP of the insulin to be purified. Particularly preferred pH values are those up to 0.5 pH units above o below the IEP.

The eluents contain a buffer substance in order to keep the pH of the eluent constant. Suitable buffer substances are known in the literature, for example phosphates, alkali metal or alkaline earth metal salts, such as sodium citrate or potassium acetate, ammonium citrate, acetate, sulfate or chloride. The eluents additionally contain water-miscible organic solvents such as, for example, alcohols, ketones, methyl acetate, dioxane, dimethyl sulfoxide or acetonitrile. Alcohols such as n- or iso-propanol, methanol or ethanol, or methyl acetate, are preferred.

The concentration of the water-miscible organic solvents is between 1 and 90%, preferably between 10 and 60%, particularly preferably between 10 and 35%. The concentration of the buffer substance is between 1 mmol/l and 2 mol/l, based on water as solvent, preferably between 25 mmol/l and 1 mol/l. The concentration of the zwitterions can vary within a wide range. Advantageous amounts are between 10 mmol/l and 1 mol/l, based on water as solvent, preferably between 20 mmol/l and 500 mmol/l.

The temperature during the chromatography is between 0° C. and 50° C., preferably between 15° and 30° C., particularly preferably between 15° and 20° C. The operating pressure during the chromatography is substantially constant. The chromatography can be carried out with a variable pressure, for example the chromatography can be carried out under a pressure of 5 to 400 bar, in particular under 20 to 100 bar.

The loading of the columns, chromatography and elution of the insulins and insulin derivatives are carried out by known, conventional industrial methods. The loading of the column with the solution of the insulin to be purified is preferably carried out with aqueous-alcoholic or pure aqueous buffer solution. The insulin solution has a protein content between 1 and 10%, preferably 3%.

The elution of the insulins in the process according to the invention is carried out at a constant concentration of the buffer substances (isocratically) or by altering the content of water-miscible organic solvent in the buffer. The content of organic solvent is altered so that the concentration of the organic solvent which is used increases as a function of the elution volume, specifically preferably as a linear function.

The removal of the insulin from the eluates after the chromatography is brought about by precipitation with zinc or by crystallization. In this connection it is possible either for the solvent to be removed substantially from the solution by vacuum distillation or for its concentration to be reduced by dilution with water. In any event, the solvent concentration before the precipitation or crystallization should be 10% or below in order to keep the protein content in the supernatant at <50 mg/l. The resulting pure insulin precipitates can be isolated by decantation, centrifugation or filtration, and be dried.

The process according to the invention is suitable not only for analytical chromatography but also for preparative chromatography, especially when the process according to the invention is carried out with a preparative HPLC system.

The term "preparative chromatography" means a purification process with the aim of obtaining, and not merely analyzing, pure products. The amount of the pure products can vary within wide limits, for example from 1 mg to 50 kg, preferably between 50 mg and 15 kg.

The process according to the invention is described in detail in the examples which follow. Unless otherwise indicated, percentage data relate to weight.

EXAMPLE 1

Buffer A: 0.2M ammonium sulfate, 0.1M glycine, 0.05M sodium citrate, pH 5.5, pure aqueous;

Buffer B: 0.1M ammonium sulfate, 0.1M glycine, 0.05M sodium citrate, pH 5.5, water/n-propanol in the ratio 1:1.
Sorbent: Nucleosil C18, 15–25 μm spherical, 100 Å pore width, supplied by Macherey & Nagel, Düren;
Column dimensions: 40 mm×250 mm.

The column is loaded with 3.5 g of human insulin (HI) obtained from human insulin B30-di-tert.butyl ester/ether by cleavage with trifluoroacetic acid, and with a protein content of 79.1%. The insulin is eluted by mixing buffer solutions A and B using a suitable high-pressure pump with a mixing device, so that a propanol gradient from 14 to 20% is generated. The insulin is eluted at about 17.5% propanol after 23 minutes, pumping at 46 ml/min.

Fractionation and isolation of crystallized human insulin (HI) results in a product containing 97% protein in a yield of 88.5% in the main fraction and a yield of 7.5% of a second fraction with a protein content of 85.7%. The total recovery is thus 96.0% of the original insulin.

EXAMPLE 2

Buffer A: 0.1M ammonium sulfate, 0.1M glycine, 0.025M sodium citrate, pH 5.5, pure aqueous;
Buffer B: 0.05M ammonium sulfate, 0.1M glycine, 0.025M sodium citrate, pH 5.5, water/n-propanol in the ratio 1:1.
Sorbent: Nucleosil C18-P, 15–25 μm spherical, 100 Å pore width, supplied by Macherey & Nagel;
Column dimensions: 40 mm×250 mm.

The column is loaded with 7.0 g of human insulin (HI) (protein content 86.1%) from an ester cleavage of human insulin di-tert.butyl ester/ether in the form of a 3% strength solution in 0.1M glycine/HCl buffer, pH 2.8, using a high-pressure pump. The elution is then carried out with the buffer solutions described above under pressure in the n-propanol gradient. The propanol concentration increases from 14 to 17.5% over the course of 60 minutes. Fractionation and crystallization in the manner described above results in a product with a protein content of 98.7%. The yield of purified human insulin is 91% of the insulin employed.

EXAMPLE 3

Buffer A: 0.1M ammonium sulfate, 0.1M glycine, 0.025M sodium acetate, pH 5.5, pure aqueous;
Buffer B: 0.05M ammonium sulfate, 0.1M glycine, 0.025M sodium acetate, pH 5.5, water/n-propanol in the ratio 1:1.
Sorbent: Lichrospher Select B, C8, 15–25 μm, 60 Å pore width, supplied by Merck.
Column dimensions: 50 mm×250 mm.

The column is loaded with a solution of 10 g of reaction mixture from the transamidation of pig insulin with trypsin, dissolved in 200 ml of 0.1M glycine/HCl buffer, pH 2.8. The individual protein components are eluted separately over the course of 120 minutes at a flow rate of 40 ml/min while increasing the propanol concentration from 14 to 30%. The main fraction obtained after crystallization or precipitation and drying is human insulin B30-di-tert.butyl threonine ester/ether with a purity 97% and a yield if 93% based on the insulin employed.

EXAMPLE 4

Buffer A: 0.1M sodium chloride, 0.1M glycine, 0.025M sodium acetate, pH 5.5, pure aqueous;
Buffer B: 0.05M sodium chloride, 0.1M glycine, 0.025M sodium acetate, pH 5.5, water/n-propanol in the ratio 1:1.
Sorbent: Zorbax Pro10, C8, 10 μm, supplied by DuPont.
Column dimensions: 5 cm×25 cm.

7.5 g of HI from cleavage of human insulin B30-di-tert.butyl threonine ester/ether with trifluoroacetic acid in 100 ml of 0.1M glycine/HCl solution were pumped onto the column and eluted at a flow rate of 80 ml/min. The concentration of buffer B increased from 18 to 25% over the course of 60 minutes. The retention time (RT) was about 37 minutes in this case. 96.8% of the initial HI was isolated with a purity >97% from the main fraction after crystallization and drying, and the second fraction contained 2.2% HI of <50% purity.

EXAMPLE 5

Buffer A: 0.2M sodium sulfate, 0.1M glycine, 0.03M ammonium acetate, pH 5.5, 10% methyl acetate;
Buffer B: 0.05M sodium sulfate, 0.1M glycine, 0.03M ammonium acetate, pH 5.5, 20% methyl acetate;
Sorbent: Kromasil C8, 13 μm, 100 Å pore width, supplied by EKA Nobel.
Column dimensions: 5 cm×25 cm.

8 g of bovine insulin per liter of column volume were applied with the aid of 0.1M glycine/HCl buffer to the column—equilibrated with 30% buffer B. The buffer B concentration increased to 80% (=18% methyl acetate) over the course of 90 minutes; bovine insulin eluted after 65 minutes with a purity >97.5% in the main fraction (63.5% yield) and was precipitated with zinc chloride after dilution with water. The total recovery was 92.5%.

EXAMPLE 6

Buffer A: 0.1M ammonium sulfate, 0.1M glycine, 0.025M sodium acetate, pH 5.5, 5% n-propanol;
Buffer B: 0.05M ammonium sulfate, 0.1M glycine, 0.025M sodium acetate, pH 5.5, water/n-propanol in the ratio 1:1.
Sorbent: Kromasil C8, 13 μm, 100 Å pore width, supplied by EKA Nobel.
Column dimensions: 5 cm×25 cm.

The column was loaded with 4 g (=8 g/l) of human insulin from cleavage of human insulin B30-di-tert.butyl threonine ester/ether with trifluoroacetic acid, with a purity of about 92%. In a gradient from 18 to 25% buffer B over the course of 90 minutes, the human insulin eluted after 45 minutes with a purity >97% in the main fraction (yield 91.8%) and 80.5% in the second fraction (yield 4.7%).

EXAMPLE 7

Buffer A: 0.1M ammonium sulfate, 0.1M glycine, 0.025M sodium acetate, pH 5.5, 10% n-propanol;
Buffer B: 0.05M ammonium sulfate, 0.1M glycine, 0.025M sodium acetate, pH 5.5, water/n-propanol in the ratio 1:1.
Sorbent: Kromasil C8, 13 μm, 100 Å pore width, supplied by EKA Nobel.
Column dimensions: 10 cm×40 cm.

18 g of pig insulin were introduced onto the column in 1.8 l of 0.1M glycine/HCl buffer, pH 3.0, with 5% n-propanol. The gradient changed from 9% buffer B (=13.6% n-propanol) to 11% buffer B (=14.4% n-propanol) in 70 minutes. Pig insulin eluted after 50 minutes with a protein content >98% in the main fraction (89% yield). The total recovery was 96.8% of the initial amount.

EXAMPLE 8

Buffer A: 0.2M ammonium chloride, 0.1M glycine, 0.025M sodium citrate, 5% n-propanol, pH 5.5;
Buffer B: as buffer A, but 50% n-propanol added.
Sorbent: Kromasil C8, 13 μm, 100 Å pore width, supplied by EKA Nobel, Sweden.
Column dimensions: 50 mm×250 mm.

4 g of genetically engineered human insulin (protein content 89.5%) are dissolved in 0.1M glycine buffer, pH 3.0, as 2% strength protein solution and pumped onto the column by a high-pressure pump. Elution is carried out by a linear gradient from 13% to 16% n-propanol over the course of 70 minutes at a flow rate of 80 ml/min. Fractionation and crystallization results in a human insulin with a protein content of 98% in the main fraction with a yield of 93%. The total recovery is 98% based on the initial amount.

EXAMPLE 9

Buffer A: 0.2M ammonium sulfate, 0.1M glycine, 0.025M ammonium citrate, 5% ethanol, pH 5.5;
Buffer B: as buffer A but 50% ethanol added.
Sorbent: Kromasil C8, 10 μm, 100 Å pore width, supplied by EKA Nobel, Sweden.
Column dimensions: 50 mm×250 mm.

4.5 g of genetically engineered human insulin (protein content 86.2%) are dissolved in 250 ml of glycine buffer, pH 3.0, and then pumped onto the column. The protein is chromatographed by generating a linear gradient from the two buffers A and B with two high-pressure pumps. Elution takes place after 100 minutes at an ethanol concentration of 33% and a constant flow rate of 80 ml/min. Fractionation and crystallization result in a human insulin with a protein content of 96% in the main fraction, the total recovery being 93% based on the initial material.

EXAMPLE 10

Buffer A: 0.2M ammonium chloride, 0.1M glycine, 0.025M sodium citrate, 10% methyl acetate, pH 5.5;
Buffer B: same salt concentration as in buffer A but 20% methyl acetate.
Sorbent: Kromasil C8, 10 μm, 100 Å pore width, supplied by EKA Nobel, Sweden.

4.6 g of crude human insulin derived from the working up of genetically engineered insulin are dissolved in 200 ml of aqueous glycine buffer and then pumped onto a 50×250 mm HPLC column for the chromatography. The column material is previously equilibrated at a methyl acetate concentration of 13% methyl acetate by mixing buffers A and B using two high-pressure pumps. After loading, the human insulin is eluted by a linear gradient from 13% to 17% methyl acetate over the course of 90 minutes. The main product is isolated by crystallization from the elution solution. This results in 3.8 g of human insulin with a protein content of 96%. The total recovery based on the starting material is 90% in this case.

EXAMPLE 11

Buffer A: 0.2M ammonium sulfate, 0.1M betaine, 0.05M citric acid, pH 5.5 with sodium hydroxide solution (pure aqueous);
Buffer B: 0.1M ammonium sulfate, 0.1M betaine, 0.05M citric acid, pH 5.5 with sodium hydroxide solution (water/isopropanol ratio 1:1);
Sorbent: Nucleosil C 18, 15-25 μm spherical, 100 Å;
Column: 40 mm×250 mm.
Flow rate: 45 ml/min.

The column was loaded with 3 g (protein content 79%) of human insulin from an ester cleavage of human insulin di-tert.butyl ester/ether in the form of a 3% strength solution in 0.1M betaine/HCl buffer, pH 3.0, using a high-pressure pump. This was followed by isocratic elution at 44% buffer B with the abovementioned buffer system. The retention time was about 35 minutes. Fractionation resulted in 98.1% human insulin in the main fraction in a yield of 80.5%. The total recovery was 90.5%.

EXAMPLE 12

Buffer A: 0.1M ammonium sulfate, 0.1M glutamic acid, 0.05M citric acid, pH 5.5 with sodium hydroxide solution (pure aqueous);
Buffer B: 0.1M ammonium sulfate, 0.1M glutamic acid, 0.05M citric acid, pH 5.5 with sodium hydroxide solution (water/n-propanol: 1:1);
Sorbent: Nucleosil C18-P, 15-25 μm spherical, 100 Å;
Column: 50 mm×250 mm.
Flow rate: 60 ml/min.

The column was loaded with 6 g (protein content 73%) of human insulin from an ester cleavage of human insulin di-tert.butyl ester/ether in the form of a 3% strength solution in 0.1M acetic acid, pH 3.0, using a high-pressure pump. Elution was then carried out with the abovementioned buffer system at a gradient of 25%-28% buffer B. The retention time was about 25 minutes. Fractionation resulted in 98.6% human insulin in the main fraction in a yield of 65%. The total recovery was 88.5%.

EXAMPLE 13

Buffer A: 0.15M ammonium sulfate, 0.10M triethylamine, pH 6.5 with sulfuric acid (pure aqueous);
Buffer B: 0.08M ammonium sulfate, 0.05M triethylamine, pH 6.5 with sulfuric acid (water/2-propanol: 1:1);
Sorbent: Nucleosil C18-P, 15-25 μm spherical, 100 Å;
Column: 50 mm×250 mm.
Flow rate: 60 ml/min.

The column was loaded with 5 g of human insulin from cleavage of human insulin di-tert.butyl threonine ester/ether with trifluoroacetic acid in a 3% strength solution and then eluted between 32 and 42% buffer B. The retention time was 40 minutes. Fractionation and crystallization resulted in 72% in the main fraction with a purity of 92.7%. The total recovery was 76% of the initial amount.

EXAMPLE 14

Buffer A: 0.1M citric acid, 0.2M ammonium sulfate, pH 2.5 with hydrochloric acid, pure aqueous.
Buffer B: 0.1M citric acid, 0.1M ammonium sulfate, pH 2.5 with hydrochloric acid, water/n-propanol: 1:1.
Sorbent: Nucleosil C18, supplied by Macherey & Nagel.
Column: 40-250 mm.
Flow rate: 45 ml/min.

The column was loaded with 3 g of human insulin from cleavage of human insulin di-tert.butyl threonine ester/ether with trifluoroacetic acid in the form of a 3% strength solution in 0.1M glycine buffer, pH 3.0, and then eluted between 34 and 35% buffer B. The retention time was 45 minutes. Fractionation, crystallization and drying resulted in isolation of 57% of the initial amount in the main fraction, with a purity of 94.8% and 16% in the second fraction (purity 84%).

EXAMPLE 15

Buffer A: 0.1M citric acid, 0.2M ammonium sulfate, pH 3.5 with hydrochloric acid, pure aqueous.
Buffer B: 0.1M citric acid, 0.1M ammonium sulfate, pH 3.5 with hydrochloric acid, water/n-propanol, 1:1.
Sorbent: Nucleosil C18, supplied by Macherey & Nagel.
Column: 40×250 mm.
Flow rate: 45 ml/min.

The column is loaded as in Example 14. The retention time was about 40 minutes. Fractionation, crystallization and drying resulted in 51% of the initial human insulin employed being found in the main fraction with a purity of 97.5%, and 4% being found in the second fraction (68% purity).

EXAMPLE 16

Buffer A: 0.1M tris, 0.1M glycine, 0.1M ammonium chloride, pH 8.5 with hydrochloric acid, pure aqueous;
Buffer B: 0.1M tris, 0.1M glycine, 0.1M ammonium chloride, pH 8.5 with hydrochloric acid, water/n-propanol: 1:1.
Sorbent: Kromasil C8, 13 μm, 100 Å.
Column: 50 mm×250 mm.
Flow rate: 60 ml/min.

The column was equilibrated to 33% buffer B and loaded with 6 g of human insulin from cleavage with trifluoroacetic acid (see Example 14) in the form of a 3% strength solution in 0.1M tris buffer, pH 8.5. Elution took place after about 35 minutes. The main fraction after fractionation and crystallization contained 96.6% pure human insulin in a yield of 86%. The total recovery was 95%.

EXAMPLE 17

Buffer A: 0.1M ammonium chloride, 0.025M citric acid, pH 5.5 with ammonia, 5% by volume n-propanol.
Buffer B: 0.1M ammonium chloride, 0.025M citric acid, pH 5.5 with ammonia, 50% by volume n-propanol.
Sorbent: Kromasil C8, 13 μm, 100 Å.
Column: 50 mm×250 mm.
Flow rate: 60 ml/min.

The column was loaded as already described with 6 g of human insulin from cleavage with trifluoroacetic acid (see Example 14). Insulin was eluted with a retention time of 40 minutes within a gradient from 21% to 25% buffer B in 60 minutes. The main fraction contained 91% of the initial product with a purity of 97.5%. The total recovery was 96%.

EXAMPLE 18

Buffer A: 0.1M potassium chloride, 0.025M citric acid, pH 5.5 with potassium hydroxide solution, 5% by volume n-propanol.
Buffer B: 0.1M potassium chloride, 0.025M citric acid, pH 5.5 with potassium hydroxide solution, 50% by volume n-propanol.
Sorbent: Kromasil C8, 13 μm, 100 Å.
Column: 50 mm×250 mm.
Flow rate: 60 ml/min.

Loading and gradient as in Example 17. Elution took place after 35 minutes. The main fraction contained 90% of the initial amount of human insulin with a purity of 96.5%. The total recovery was 93%.

EXAMPLES 19 TO 42

The chromatography in Examples 19 to 24 was carried out under the same conditions as in Example 14. There was merely a change in the buffer or the amount of zwitterion.

EXAMPLE 19

Buffer A: 0.15M ammonium sulfate, 0.1M triethylamine, pH 7.0 with sulfuric acid;
Buffer B: 0.08M ammonium sulfate, 0.05M triethylamine, pH 7.0 with sulfuric acid.
Result: 95.2% purity of the main fraction; 67% yield in the main fraction.

EXAMPLE 20

Buffer as in Example 16 but without 0.1M glycine
Result: 96.1% purity in the main fraction; 65% yield in the main fraction and 25% in the second fraction.

EXAMPLE 21

Buffer as in Example 15 with the addition of 0.1M glycine.
Result: 96% purity in the main fraction; 66% yield in the main fraction and 6% in the second fraction.

EXAMPLE 22

Buffer A: 0.1M ammonium chloride, 0.025M citric acid, pH 4.5 with ammonia, 5% by volume n-propanol, 0.1M glycine betaine.
Buffer B: as buffer A but with the addition of 50% n-propanol.
Result: 98.1% purity in the main fraction; 88% yield in the main fraction and 6% in the second fraction.

EXAMPLE 23

Buffer as in Example 22 but pH 5.4 and 0.1M glycine in place of glycine betaine.
Result: 97.9% purity in the main fraction; 92% yield in the main fraction and 8% in the second fraction.

EXAMPLE 24

Buffer as in Example 13 but pH 6.0 and addition of 0.1M glycine.
Result: 94.3% purity in the main fraction; 77% yield in the main fraction and 13% in the second fraction.

EXAMPLE 25

Table 1 summarizes the yield and purity of insulins as a function of the pH and/or zwitterion in the eluent.

TABLE 1

| pH | Zwitterion | Purity of main fraction | Yield Main fr. | Yield Second fr. | Ex. No. |
|---|---|---|---|---|---|
| 2.5 | — | 94.8 | 57 | 16 | 14 |
| 3.5 | — | 97.5 | 51 | 4 | 15 |
| 6.5 | — | 92.7 | 72 | 4 | 13 |
| 7.0 | — | 95.2 | 67 | — | 19 |
| 8.5 | — | 96.1 | 65 | 25 | 20 |
| 5.5 | — | 97.5 | 91 | 5 | 17 |
| 5.5 | — | 96.5 | 90 | 3 | 18 |
| 3.5 | Gly | 96.0 | 66 | 6 | 21 |
| 4.5 | Glycine betaine | 98.1 | 88 | 6 | 22 |
| 5.4 | Gly | 97.9 | 92 | 8 | 23 |
| 5.5 | Gly | 98.0 | 93 | 5 | 8 |

TABLE 1-continued

| pH | Zwitterion | Purity of main fraction | Yield Main fr. | Yield Second fr. | Ex. No. |
|---|---|---|---|---|---|
| 6.0 | Gly | 94.3 | 77 | 13 | 24 |
| 8.5 | Gly | 96.6 | 86 | 9 | 16 |

We claim:

1. A process for the purification of insulin and/or insulin derivatives by chromatography in aqueous, buffered solvents which contain water-miscible organic solvents, on lipophilically modified silica gel, wherein α-amino acids or betaines are dissolved in the buffered solvents and the pH of the solvent mixture is within about one pH unit above or below the isoelectronic point of the insulin or insulin derivative to be purified.

2. The process as claimed in claim 1, wherein the pH of the solvent mixture is up to 0.5 pH units below or above the isoelectric point.

3. The process as claimed in claim 1, wherein glycine, glutamic acid or glycine betaine are employed as α-amino acids or betaines.

4. The process as claimed in claim 1, wherein insulin derivatives of the formula I

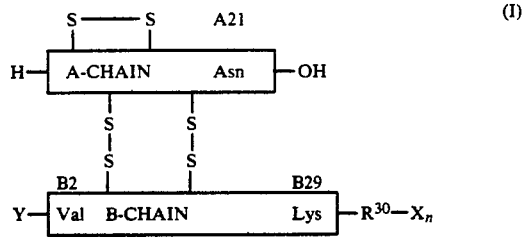

in which
R$^{30}$ is the residue of a genetically encodable L-amino acid,
X is a hydroxyl group, a physiologically acceptable organic group which is basic in nature and has up to 50 carbon atoms, a genetically encodable L-amino acid whose terminal carboxyl functionality which is present where appropriate can be free, an ester functionality, an amide functionality, a lactone or reduced to CH$_2$OH,
n is an integer from 0 to 10,
y is hydrogen or L-phenylalanine, and the A and B chains are the sequences of animal or human insulin, are used.

5. The process as claimed in claim 4, wherein in formula I R$^{30}$ is L-alanine or L-threonine and X is one or more L-amino acids from the group comprising L-arginine, L-lysine or L-phenylalanine.

6. The process as claimed in claim 1 wherein a preparative high-pressure liquid chromatography system is employed.

* * * * *